United States Patent [19]

Boulogne et al.

[11] 4,367,220
[45] Jan. 4, 1983

[54] LIPSTICK COMPOSITION AND PROCESS FOR PREPARING SAME

[75] Inventors: Jean Boulogne, L'Hay les Roses; Michel Guillon, Bourg la Reine; Christos Papantoniou, Epinay sur Seine, all of France

[73] Assignee: L'Oreal, France

[21] Appl. No.: 812,427

[22] Filed: Jul. 1, 1977

[30] Foreign Application Priority Data

Jul. 2, 1976 [FR] France .................... 76 20263

[51] Int. Cl.³ ............................................. A61K 7/025
[52] U.S. Cl. ...................................... 424/64; 260/410.6
[58] Field of Search ......................... 424/64; 260/410.6

[56] References Cited

U.S. PATENT DOCUMENTS

| | | | |
|---|---|---|---|
| 3,937,811 | 2/1976 | Papantoniou | 424/64 |
| 3,972,914 | 8/1976 | Vanlerberghe | 260/410.6 |

FOREIGN PATENT DOCUMENTS

| | | | |
|---|---|---|---|
| 2535777 | 2/1976 | Fed. Rep. of Germany | 260/410.6 |
| 1147482 | 4/1969 | United Kingdom | 260/410.6 |
| 1192080 | 5/1970 | United Kingdom | 424/64 |

*Primary Examiner*—Dale R. Ore
*Attorney, Agent, or Firm*—Stevens, Davis, Miller & Mosher

[57] ABSTRACT

Cosmetic compositions, particularly lipsticks, which contain essentially: (1) at least one liposoluble polymer having vinyl ester units; (2) at least 10% by weight 1-docosanoyloxy-3-(2-ethyl)-hexyloxy-2-propanol or a compound of the formula:

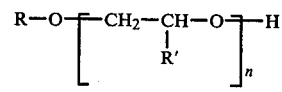

wherein: R represents a radical derived from lanolin alcohol
R' represents the radical $C_{10}H_{21}$ and n is 1.5;

(3) at least one fatty body; and (4) at least one non-toxic coloring material. Processes for preparing such compositions, and particularly for preparing 1-docosanoyloxyl-(2-ethyl)-3-hexyloxy-2-propanol are also disclosed.

12 Claims, No Drawings

LIPSTICK COMPOSITION AND PROCESS FOR PREPARING SAME

BACKGROUND

The present invention has as its object a new cosmetic composition for makeup in the form of lipsticks.

The applicant company has already proposed the utilization in embodiments of makeup, particularly of lipsticks, of certain polymers and in particular homopolymers of polyvinyl esters or polyacrylic esters as well as copolymers of vinyl esters.

In fact, it has been observed that by utilizing a certain percentage of such polymers in these products, it is possible to improve the solidity of the sticks, to provide brilliance and better adhesion as well as good persistence of the film applied to the lips.

Nevertheless, these compositions in the form of lipsticks were found to have certain disadvantages, in particular a migration of the colouring materials into the corners of the lips.

BRIEF SUMMARY OF THE INVENTION

The applicant company has recently observed that it was possible to avoid these disadvantages, which affect the esthetics of the product, by associating the previously recommended polymers with a glyceryl ester-ether or with a glycol ether.

In fact, it is possible, by the joint utilization of a polymer on the one hand and these compounds on the other, to prevent the migration of the colouring materials into the corners of the lips, and in addition to augment still further the brilliance of the film thus deposited on the lips.

DETAILED DESCRIPTION

The present invention has as its object, by way of a new industrial product, a cosmetic composition in the form of lipstick, characterized by the fact that it contains essentially:

(i) at least one fat-soluble polymer having vinyl ester units;

(ii) at least 10% by weight of 1-docosanoyloxy-3(2-ethyl)-hexyloxy-2-propanol, or a compound corresponding to the formula:

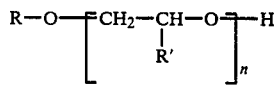

wherein
R represents a radical derived from lanolin alcohol,
R' represents the radical $C_{10}H_{21}$
and n is 1.5;

(iii) at least one fatty body, and (iv) at least one non-toxic colouring material.

The 1-docosanoyloxy-3(2-ethyl)-hexyloxy-2-propanol which associated with the polymer, prevents migration of the colouring materials into the corners of the lips has the following formula:

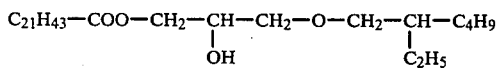

This compound is obtained by reaction of behenic acid (or docosanoic acid) with 2-ethyl-hexyl glycidyl ether.

The reaction is carried out in the presence of a basic catalyst such as sodium methoxide or sodium ethoxide, and at a temperature of the order of 130° C. for about 2 to 8 hours.

The product is isolated from the reaction mixture after several washings with water and after neutralization with a base, and is then dried at reduced pressure. The light products are eliminated at about 130° C. at $10^{-3}$ mm Hg and the desired product is then distilled at about 205° C. and at $10^{-3}$ mm Hg.

This product is solid at room temperature and has a final melting point of the order of 35°–40° C.

The compound of formula (I) above which also avoids migration of colouring materials is obtained by reacting 11-12-epoxy-dodecane with lanolin alcohol in the presence of boron trifulouride ($BF_3$).

The reaction is carried out at a temperature of the order of 80° C. for a duration of 1–2 hours.

The product is recovered after neutralization and washing with water.

This product is present in the form of a slightly yellow soft wax, whose drip point is about 40° C.

The 1-docosanoyloxy-3(2-ethyl)-hexyloxy 2-propanol or the compound of formula (I) is, as mentioned above, present in the composition at a concentration of at least 10% but preferably between 10 and 30%.

These compounds replace partly the fatty body which is either a wax or a mixture of a wax and an oil.

According to the invention, the fatty body is generally present in a proportion between 35 and 75%.

Among the waxes which can be utilized as fatty body, there can in particular be cited: ozokerite, lanolin, lanolin alcohol, hydrogenated lanolin, acetylated lanolin, lanolin wax, beeswax, Candellila wax, microcrystalline wax, Carnauba wax, cetyl alcohol, stearyl alcohol, spermaceti, cocoa butter, lanolin fatty acids, petrolatum, vaselines, mono-, di-and triglycerides which are solid at 25° C., fatty acid esters solid at 25° C., silicone waxes such as methylocatadecane-oxy-polysiloxane and poly(-dimethyl-siloxy) stearoxysiloxane, stearic monoethanolamide, colophony and its derivatives such as glycol and glycerol abietates, hydrogenated oils solid at 25° C., the sucroglycerides, and the oleates, myristates, lanolates, stearates and dihydroxystearates of calcium, magnesium zirconium and aluminum.

Among the oils which can be utilized as fatty body, there can be mentioned in particular: - paraffin oil, Purcellin oil, perhydrosqualene, sweet oil of almond, avocado oil, calophyllum oil, castor oil, horse oil, pig oil, olive oil, mineral oils having a boiling point between 310° and 410° C., silicone oils such as the dimethylpolysiloxanes, linoleyl alcohol, linolenyl alcohol, oleyl alcohol, cereal germ oils such as wheat germ oil, isopropyl lanolate, isopropyl palmitate, isopropyl myristate, butyl myristate, cetyl myristate, hexadecyl stearate, 2-ethyl hexyl stearate, butyl stearate, octyl hydroxy stearate, decyl oleate, acetylglycerides, octanoates and decanoates of alcohols and polyalcohols such as those of glycol and glycerol, the ricinoleates of alcohols and of polyalcohols such as cetyl, isostearyl alcohol, isocetyl lanolate, isopropyl adipate, hexyl lanolate, and octyldodecanol.

According to the invention, there can likewise be used as waxes or as oils, derivates of 1,2-alkanediols and in particular the fatty acid esters of 1,2-alkanediols, such as those described in French Patent No. 75-24,656 or one of the compounds described in French Patent Nos. 7,409,657 and 75-24657, the U.S. corresponding Patents are Nos. 3,972,914 and 4,126,702.

The polymers having vinyl units and utilizable in the lipsticks according to the invention should be liposoluble, that is, have a high affinity for waxes and oils. These polymers are, as indicated above, either homopolymers or copolymers and are present at a concentration of about 10 to 35% by weight. Among the homopolymers, there can be cited in particular those resulting from the homopolymerization of vinyl hexanoate, vinyl 2,2-dimethylpentanoate, vinyl octanoate, vinyl cekanoates (cekanoic acid is the commercial name of a mixture of linear and branched fatty acids having the same number of carbon atoms, namely, 8, 9, or 10), vinyl laurate, vinyl stearate and vinyl isostearate.

Among the copolymers there can be mentioned in particular those resulting from the copolymerization of vinyl acetate/allyl stearate, vinyl acetate/vinyl laurate; vinyl acetate/vinyl stearate, vinyl acetate/1-octadecene, vinyl acetate/octadecyl vinyl ether, vinyl propionate/allyl laurate, vinyl propionate/vinyl laurate, vinyl stearate/1-octadecene, vinyl stearate/ethylvinyl ether, vinyl propionate/cetyl vinyl ether, vinyl stearate/allyl acetate, vinyl 2,2-dimethyl-octanoate/vinyl laurate, allyl 2,2-dimethyl-pentanoate/vinyl laurate, vinyl dimethylpropionate/vinyl stearate, allyl dimethylpropionate/vinyl stearate, vinyl propionate/vinyl stearate, vinyl dimethylpropionate/vinyl laurate, and allyl propionate/allyl stearate.

These copolymers can, if necessary, be crosslinked by means of a cross-linking agent, which has the effect of increasing the molecular weight. Among these cross-linking agents there can be cited in particular tetraallyloxyethane, divinylbenzene, divinyl octanedioate, divinyl dodecane-dioate, and divinyl octadecanedioate.

Preferably these homopolymers and copolymers have a molecular weight between 2,000 and 500,000, and preferably between 6,000 and 300,000.

These homopolymers and copolymers of vinyl esters are described in detail in French applications Nos. 74-19,724 and 74-19,725.

The colouring materials employed in the compositions according to the invention are, of course, non-toxic to human beings, and are those utilized in current practice in formulations of the lipstick type.

They are in general present in a proportion between 2 and 30% and among them there can be cited: the eosins and other halogenated derivatives of fluorescein (bromo-acids), and particularly those known under the designations of D and C Red No. 21, D and C Red No. 27, D and C Orange No. 5, the inorganic pigments such as the oxides of iron or chromium, the ultramarines (polysulfides of amino-silicates), titanium dioxide, and the organic pigments such as: D and C Red No. 36 and D and C Orange No. 17.

Finally, there can likewise be included among the colouring materials the lakes, such as the calcium lakes of the D and C Red No. 6, 7, 21 and 27, the barium lakes of D and C Red Nos. 6 and 9, the aluminum lakes of D and C Red Nos. 21 and 27 and D and C Yellow Nos. 5 and 6, and the zirconium lakes of D and C Red No. 21 and D and C Orange No. 5.

These compositions according to the invention can, of course, likewise contain other conventional ingredients such as for example pearling agents in a proportion of 2 to 20%, perfumes, anti-solar agents, antioxidant agents, and preservatives.

Among the pearling agents there can be cited in particular bismuth oxychloride, mica-titania, and guanine crystals.

Among the anti-oxidant agents, there can be cited in particular those of the phenolic type such as the propyl, octyl and dodecyl esters of gallic acid, butylated hydroxyanisole, butylated hydroxytoluene, and nordihydroguaiaretic acid.

In certain cases, it is likewise necessary to utilize certain solvents for the insoluble colouring materials in the fatty bodies. Among these solvents, there can be mentioned: the glycols, the tetrahydrofurfuryl esters, polyethylene glycols, and monoalkanolamides.

The present invention likewise has as its object, by way of a new industrial product, 1-docosanoyloxy-3(2-ethyl) hexyloxy-2-propanol and the process of its preparation as previously described.

There will now be given by way of an illustration, and without and limitative character, an example of preparation of 1-docosanoyloxy-3(2-ethyl)-hexyloxy-2-propanol as well as several examples of cosmetic compositions in the form of lipsticks according to the invention.

EXAMPLE A: Preparation of
1-docosanoyloxy-3(2-ethyl)-hexyloxy 2-propanol

To 335 g of behenic acid (or docosanoic acid), 1.050 mole, melted in a round flask there are added with agitation 2.9 g of powdered sodium methoxide (50 meq) and the temperature is then raised to 130° C. under nitrogen.

There are then added dropwise and with agitation, 186 g (1 mole) of 2-ethyl hexyl glycidyl ether, and heating is continued for 6 hours under nitrogen at 130° C. after the end of the addition.

The extent of the reaction is determined by measuring the index of residual acid. The reaction is continued until it is about 95% complete.

The product thus obtained is washed once with 500 ml of boiling water containing the quantity of caustic soda necessary for neutralizing the residual acidity.

After the water, there are added 200 ml. of isopropanol to improve the decantation. Washing is then carried out twice with water at 80° C. about 500 ml for each washing.

Drying is then carried out in vacuo and with agitation on a boiling water-bath.

The product is then purified by molecular distillation:
(1) Elimination of the light products at 130° C. under $10^{-3}$ mm Hg
(2) Distillation of the product at 205° C. under $10^{-3}$ mm Hg
    Yield of distillation: 78%
    Overall yield: 67%
    Analyses:
    Saponification number: Theoretical, 1.98 meq/g; Found, 2.0 meq/g
    Hydroxyl number: Theoretical, 1.98 meq/g; Found, 1.85 meq/g
    Acid number: Nil.
    Final melting point: 35° C.

EXAMPLE B: Preparation of the compound of formula (I) above.

To 740 g (2 moles) of lanolin alcohol which has been previously melted at about 80° C. one adds 5.2 ml of a BF$_3$/ether complex and thereafter one adds drop by drop, for a duration of about one hour, 552 g (3 moles) of −11,12 epoxy dodecane. The temperature is maintained at 80° C. for about 10 minutes after completion of the addition so that all of the added epoxide is consumed.

The product thus obtained is washed with water containing the quantity of soda necessary for neutralizing the acidity due to the catalyst. The organic phase separated after decantation is washed three more times with hot water.

The product then is recovered with its weight of water which one distills to eliminate removable impurities than the product is totally dehydrated under reduced pressure.

One thus obtains the product of formula (I) above in the form of a soft wax, slightly yellow. Drip point=40° C. Index of OH=1.90 meq/g (theoretically: 1.55).

EXAMPLES OF LIPSTICKS

Example 1

There is prepared according to the invention a lipstick, by proceeding to mix the following ingredients:

| | |
|---|---|
| Microcrystalline wax | 12 g |
| Acetylated lanolin | 5.9 g |
| Lanolin | 10 g |
| Hydrogenated lanolin | 10 g |
| Lanolin alcohols | 11 g |
| Butylated hydroxyanisole | 0.1 g |
| Copolymer of 31.3% vinyl acetate/68.7% allyl stearate | 8 g |
| Homopolymer, polyvinyl laurate | 15 g |
| 1-docosanoyloxy-3(2-ethyl)hexyloxy-2-propanol | 15 g |
| Colouring materials: | |
| Titanium oxide | 1 g |
| Al lake of D and C Red 27 | 7.5 g |
| D and C Red 36 | 1 g |
| Al lake of D and C Yellow 6 | 2.5 g |
| Perfume | 1 g |
| | 100 g |

Example 2

There is prepared according to the invention, a lipstick by mixing the following ingredients:

| | |
|---|---|
| Microcrystalline wax | 9 g |
| Acetylated lanolin | 9 g |
| Oleyl alcohol | 11 g |
| Liquid lanolin | 8 g |
| Mineral oil | 10.9 g |
| Butylated hydroxytoluene | 0.1 g |
| Copolymer, 31.3% vinyl acetate/68.7% allyl stearate | 10 g |
| Homopolymer, vinyl laurate | 11 g |
| 1-docosanoyloxy-3(2-ethyl)hexyloxy-2-propanol | 20 g |
| Colouring materials: | |
| Titanium oxide | 3.5 g |
| Zirconium lake of D and C Red 21 | 3.5 g |
| Calcium lake of D and C Red 6 | 0.2 g |
| D and C Red 36 | 1.5 g |
| Al lake of D and C Yellow 6 | 1.5 g |
| Perfume | 0.8 g |
| | 100 g |

Example 3

A lipstick is prepared according to the invention, by proceeding to mix the following ingredients:

| | |
|---|---|
| Ozokerite | 15 g |
| Lanolin | 8 g |
| Mineral oil | 3 g |
| Oleyl alcohol | 5 g |
| Triglycerides | 3 g |
| Castor oil | 8.4 g |
| Butylated hydroxytoluene | 0.1 g |
| Copolymer, 31.3% vinyl acetate/68.7% allyl stearate | 10 g |
| Homopolymer, polyvinyl laurate | 10 g |
| 1-docosanoyloxy-3(2-ethyl)hexyloxy-2-propanol | 15 g |
| Colouring materials: | |
| Al lake of D and C Red 27 | 1 g |
| Ca lake of D and C Red 27 | 1 g |
| D and C Red 36 | 1 g |
| D and C Red 6 | 6 g |
| Al lake of D and C Yellow 5 | 1 g |
| Mica-titania | 11 g |
| Perfume | 1.5 g |
| | 100 g |

Example 4

A lipstick is prepared according to the invention, by proceeding to mix the following ingredients:

| | |
|---|---|
| Microcrystalline wax | 8 g |
| Liquid lanolin | 10 g |
| Mineral oil | 4 g |
| Acetylated lanolin | 6.9 g |
| Hydrogenated palm oil | 6 g |
| Compound of formula: R—COO—CH$_2$—CH(OH)—R' | 5 g |
| R = C$_{15}$H$_{31}$ Melting point = 55–60° C. | |
| R' = C$_{12}$/C$_{14}$ | |
| Butylated hydroxyanisole | 0.1 g |
| Copolymer, 31.3% vinyl acetate/68.7% allyl stearate | 15 g |
| Homopolymer, polyvinyl laurate | 10 g |
| 1-Docosanoyloxy-3(2-ethyl)hexyloxy-2-propanol | 1 g |
| Colouring materials: | |
| Titanium oxide | 3.75 g |
| Al lake of D and C Red 27 | 1.25 g |
| D and C Red 30 | 1 g |
| Al lake of D and C Yellow 6 | 1 g |
| Bi oxychloride | 12 g |
| Perfume | 1 g |
| | 100 g |

Example 5

A lipstick is prepared according to the invention, by proceeding to mix the following ingredients:

| | |
|---|---|
| Ozokerite | 4 g |
| Microcrystalline wax | 6 g |
| Acetylated lanolin | 10 g |
| Castor oil | 10 g |
| Hydrogenated coconut oil | 10 g |
| Lanolin alcohols | 3.9 g |
| Compound of formula: R—COO CH$_2$—CH(OH)—R' | 6 g |

| | |
|---|---|
| R = $C_{15}H_{31}$ Melting point 55-60° C. | |
| R' = $C_{12}/C_{14}$ Acid number 0.02 meq/g | |
| Butylated hydroxy-toluene | 0.1 g |
| Copolymer, vinylacetate 31.3% | |
| Allyl stearate 68.7% | 8 g |
| Homopolymer, polyvinyl laurate | 16 g |
| 1-Docosanoyloxy-3(2-ethyl) hexyloxy-2-propanol | 15 g |
| Colouring materials: | |
| Titanium oxide | 6.5 g |
| Ca lake of D and C Red 7 | 0.5 g |
| D and C Red 36 | 0.5 g |
| Black oxide of Fe | 0.4 g |
| Al lake of D and C Yellow 5 | 2.6 g |
| Perfume | 0.5 g |
| | 100 g |

Example 6

A lipstick is prepared according to the invention by proceeding to mix the following ingredients:

| | |
|---|---|
| Polyvinyl laurate | 17,0 g |
| Copolymer vinyl acetate 31.3% allyl stearate 68,7% | 8,75 g |
| Microcrystalline wax | 8,75 g |
| Di-terbutyl para-cresol | 0,1 g |
| Compound of formula (I) prepared as in Example B | 17,5 g |
| Compound of formula: R—COO CH$_2$—CH—R'<br>                                     OH | 4,35 g |
| R = $C_{15}H_{31}$ | |
| R' = $C_{12}/C_{14}$ Melting point = 55-60° C. | |
| Butyl ricinoleate | 13 g |
| Acetoglyceride | 4,35 g |
| Acetylated lanolin | 4,35 g |
| Oleic alcohol | 4,35 g |
| Lanolin liquid | 4,35 g |
| Colouring materials: | |
| Titanium oxide | 3 g |
| Al lake of D and C Red 21 | 1 g |
| Ca lake of D and C Red 7 | 0,2 g |
| D and C Red 6 | 2,5 g |
| Yellow iron oxide | 1,1 g |
| Black iron oxide | 0,35 g |
| Al lake of D and C Yellow 5 | 4,5 g |
| Perfume | 0.5 g |
| | 100 g |

Example 7

A lipstick is prepared according to the invention by proceeding to mix the following ingredients:

| | |
|---|---|
| Polyvinyl laurate | 9,2 g |
| Polyethylene grease (PM = 1.500) | 33 g |
| 1-docosanoyloxy-3(2-ethyl) hexyloxy-2-propanol | 14 g |
| Compound of formula: R—COO—CH$_2$—CH—R'<br>                                      OH | 4 g |
| R = $C_{15}H_{31}$ | |
| R' = $C_{12}/C_{14}$ Melting point = 55-60° C. | |
| Lanolin | 9,7 g |
| Lanolin liquid | 10,5 g |
| Amyl para-dimethylamino-benzoate | 1 g |
| D-Panthenol | 1 g |
| Oil of Calendula | 8 g |
| Polyethylene wax | 2 g |
| Di-tertbutyl para-cresol | 0,1 g |
| Mineral oil | 3 g |
| Colouring materials: | |
| Al lake of D and C Red 21 | 0,2 g |
| D and C Red 6 | 0,5 g |
| Yellow iron oxide | 0,3 g |
| Black iron oxide | 0,4 g |
| Al lake of D and C Yellow 5 | 2,5 g |
| Perfume | 0,6 g |
| | 100 g |

Example 8

A lipstick is prepared according to the invention by proceeding to mix the following ingredients:

| | |
|---|---|
| Polyvinyl laurate | 7 g |
| Polyethylene grease | 27 g |
| Compound of formula (I) prepared as in Example B | 9,5 g |
| Compound of formula: R—COO—CH$_2$—CH—R'<br>                                      OH | 3,5 g |
| R = $C_{15}H_{31}$ R' = $C_{12}/C_{14}$ | |
| Lanolin | 9,0 g |
| Acetylated lanolin | 9,5 g |
| Mineral oil | 9,5 g |
| Polyethylene wax | 3,5 g |
| Tertbutyl anisole | 0,1 g |
| Butyl ricinoleate | 6,4 g |
| Octyl hydroxystearate | 6,5 g |
| Colouring materials: | |
| Titanium oxide | 2 g |
| Al lake of D and C Red 27 | 2 g |
| Ca lake of D and C Red 7 | 1 g |
| D and C Red 6 | 3 g |
| Perfume | 0,5 g |
| | 100 g |

Example 9

A lipstick is prepared according to the invention by proceeding to mix the following ingredients:

| | |
|---|---|
| Polyvinyl laurate | 28 g |
| Copolymer, vinyl acetate 31,3% allyl stearate 68,7% | 4,8 g |
| Polyethylene grease | 33 g |
| 1-docosanoyloxy-3(2-ethyl) hexyloxy-2-propanol | 19,3 g |
| Compound of formula: R—COO—CH$_2$—CH—R'<br>                                    OH | 1 g |
| R = $C_{15}H_{31}$ | |
| R' = $C_{12}/C_{14}$ Melting point = 55-60° C. | |
| Tertbutyl-anisole | 0,1 g |
| Acetylated lanolin | 4,8 g |
| Mineral oil | 4,8 g |
| Colouring materials: | |
| Al lake of D and C Red 21 | 0,6 g |
| D and C Red 36 | 0,3 g |
| D and C Red 30 | 0,5 g |
| D and C Red 13 | 0,2 g |
| Al lake of D and C Yellow 5 | 2 g |
| Perfume | 0,6 g |
| | 100 g |

What is claimed is:

1. A cosmetic composition for lipsticks, comprising:
   (a) at least one liposoluble polymer having vinyl ester units;
   (b) at least 10% by weight of 1-docosanoyloxy-3 (2-ethyl)-hexyloxy-2-propanol
   (c) at least one fatty body;
   (d) at least one non-toxic coloring material.

2. The composition of claim 1, wherein the polymer having vinyl ester units is a homopolymer resulting from the homopolymerization of a monomer selected from the group consisting of vinyl hexanoate, vinyl 2,2-dimethyl-pentanoate, vinyl octanoate, the vinyl cekanoates, vinyl laurate, vinyl stearate, and vinyl isostearate.

3. The composition of claim 1, wherein the polymer having the vinyl ester units is a copolymer selected from the group consisting of copolymers of: vinyl acetate/vinyl laurate, vinyl acetate/vinyl stearate, vinyl acetate/1-octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyl-octanoate/vinyl laurate, allyl 2,2-dimethyl-pentanoate/vinyl laurate, vinyl dimethylpropionate/vinyl stearate, allyl dimethylpropionate/vinyl stearate, vinyl propionate/vinyl stearate, vinyl dimethyproprionate/vinyl laurate, and allyl propionate/allyl stearate.

4. The composition of claim 1, wherein the polymer has been crosslinked by using a crosslinking agent selected from the group consisting of tetrallyloxyethane, divinylbenzene, divinyl octanedionate, divinyl dodecanedioate, and divinyl octadecanedioate.

5. The composition of claim 1 wherein the polymer is present in a proportion of about 10 to 35% by weight of said composition.

6. The composition of claim 1 wherein the 1-docosanoyloxy-3 (2-ethyl)-hexyloxy-2-propanol is present in a proportion of 10 to 30% by weight of said composition.

7. The composition of claim 1 wherein the fatty body is a wax or oil, or a mixture thereof.

8. The composition of claim 7, wherein the fatty body is present in a proportion of 35 to 75% by weight of said composition.

9. The composition of claim 1 wherein the non-toxic coloring material is present in the composition in a concentration of 2 to 30% by weight of said composition.

10. The compound 1-docosanoyloxy-3(2-ethyl) hexyloxy-2-propanol, corresponding to the formula:

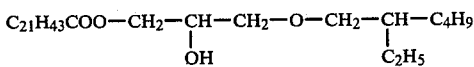

11. The compound of claim 10, having a final melting point of about 35°–40° C.

12. The composition of claim 1, which also comprises a cosmetic ingredient selected from the group consisting of a pearling agent, a perfume, an anti-solar agent, an anti-oxidant agent, a preservative and a solvent for the insoluble coloring materials in the fatty bodies.